US009598730B2

(12) United States Patent
Del-Favero et al.

(10) Patent No.: US 9,598,730 B2
(45) Date of Patent: Mar. 21, 2017

(54) FETAL CHROMOSOMAL ANEUPLOIDY DIAGNOSIS

(71) Applicant: MULTIPLICOM NV, Niel (BE)

(72) Inventors: Jurgen Del-Favero, Tienen (BE); Dirk Goossens, Antwerp (BE); Lien Heyrman, Burcht (BE)

(73) Assignee: MULTIPLICOM NV, Niel (BE)

( * ) Notice: Subject to any disclaimer, the term of this patent is extended or adjusted under 35 U.S.C. 154(b) by 310 days.

(21) Appl. No.: 14/352,755

(22) PCT Filed: Oct. 18, 2012

(86) PCT No.: PCT/IB2012/002091
§ 371 (c)(1),
(2) Date: Apr. 18, 2014

(87) PCT Pub. No.: WO2013/057568
PCT Pub. Date: Apr. 25, 2013

(65) Prior Publication Data

US 2014/0272979 A1 Sep. 18, 2014

Related U.S. Application Data

(60) Provisional application No. 61/548,632, filed on Oct. 18, 2011.

(51) Int. Cl.
*C12P 19/34* (2006.01)
*C12Q 1/68* (2006.01)

(52) U.S. Cl.
CPC ........... *C12Q 1/6869* (2013.01); *C12Q 1/686* (2013.01); *C12Q 1/6883* (2013.01); *C12Q 2600/156* (2013.01); *C12Q 2600/16* (2013.01)

(58) Field of Classification Search
USPC ................................................ 435/6.12, 91.2
See application file for complete search history.

(56) References Cited

U.S. PATENT DOCUMENTS 6,258,540 B1 7/2001 Lo et al.
7,332,277 B2 2/2008 Dhallan
7,645,576 B2 * 1/2010 Lo ........................ C12Q 1/6851 435/6.11
8,195,415 B2 6/2012 Fan et al.
8,296,076 B2 10/2012 Fan et al.
8,442,774 B2 5/2013 Lo et al.
8,663,921 B2 3/2014 Mitchell et al.
8,706,422 B2 4/2014 Lo et al.
2005/0074787 A1 * 4/2005 Fan ..................... C12Q 1/6827 435/6.11
2008/0050730 A1 * 2/2008 Modiano .......... G01N 33/57426 435/6.14
2012/0108460 A1 5/2012 Quake et al.
2012/0219950 A1 8/2012 Oliphant et al.
2012/0264121 A1 10/2012 Rava et al.
2013/0022973 A1 1/2013 Hansen et al.
2013/0130923 A1 5/2013 Ehrich et al.
2014/0186827 A1 7/2014 Pieprzyk et al.

FOREIGN PATENT DOCUMENTS

WO WO2007147074 A2 12/2007
WO WO2007147079 A2 12/2007

OTHER PUBLICATIONS

International Search Report and Written Opinion of PCT/IB2012/002091, mailed Feb. 22, 2013.
Liao, Gary J.W. et al., "Targeted massively parallel sequencing of maternal plasma DNA permits efficient and unbiased detection of fetal alleles" (2010) Clinical Chemistry, vol. 57, No. 1, pp. 92-101.
Lo, Dennis, Y.M. et al., "Plasma placental RNA allelic ratio permits noninvasive prenatal chromosomal aneuploidy detection" (2007), Nature Medicine, vol. 13, No. 2, pp. 218-223 (Abstract Only).

* cited by examiner

*Primary Examiner* — Kenneth Horlick
(74) *Attorney, Agent, or Firm* — Arent Fox LLP

(57) ABSTRACT

The invention relates to prenatal detection methods using non-invasive techniques. In particular, it relates to prenatal diagnosis of a fetal chromosomal aneuploidy by detecting fetal and maternal nucleic acids in a maternal biological sample. More particularly, the invention applies multiplex PCR to amplify selected fractions of the respective chromosomes of maternal and fetal chromosomes. Respective amounts of suspected aneuploid chromosomal regions and reference chromosomes are determined from massive sequencing analysis followed by a statistical analysis to detect a particular aneuploidy.

10 Claims, 5 Drawing Sheets

FETAL CHROMOSOMAL ANEUPLOIDY DIAGNOSIS

CROSS-REFERENCE TO RELATED APPLICATIONS

Figure 1:
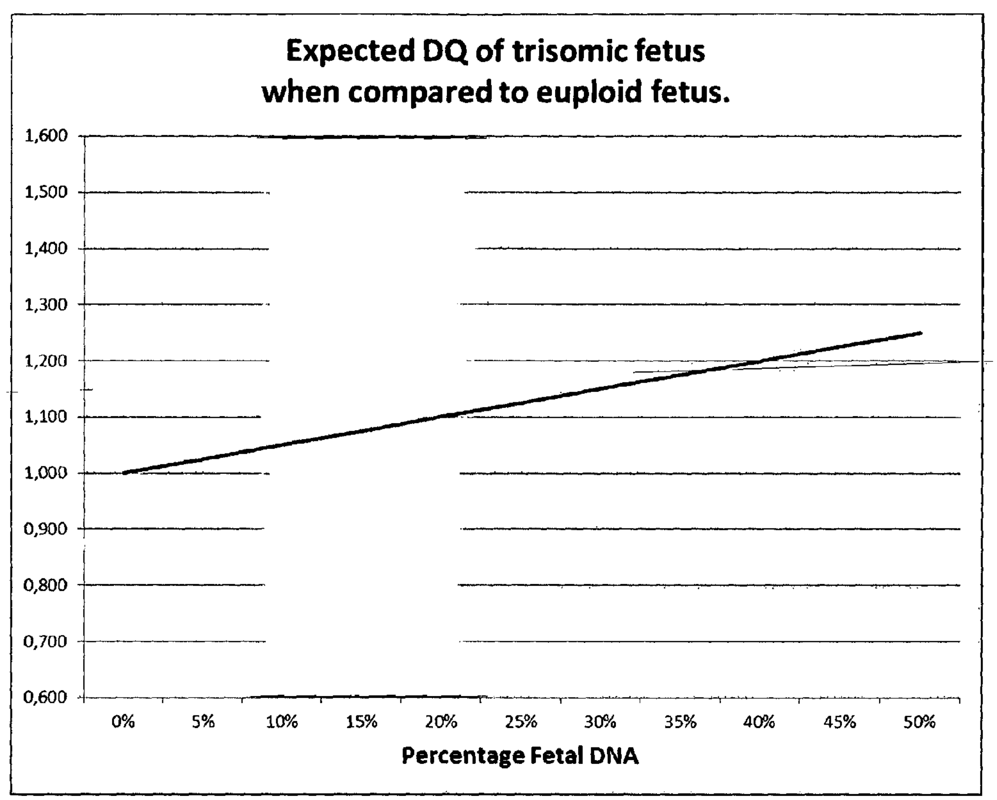

This application is the national phase application of International Patent Application Number PCT/IB2012/002091, filed Oct. 18, 2012, which claims the benefit of U.S. Provisional Patent Application No. 61/548,632 filed Oct. 18, 2011, the contents of each are hereby incorporated by reference in their entireties.

FIELD OF THE INVENTION

This invention generally relates to the diagnostic testing of a fetal chromosomal aneuploidy by determining imbalances between different nucleic acid sequences, and more particularly to the identification of aneuploidy in chromosomes 13, 18, 21, X and/or Y via testing a maternal sample such as blood.

INTRODUCTION TO THE INVENTION

Aneuploidy refers to an abnormal number of chromosomes (or part of chromosomes) that is a common cause of birth defects. In aneuploidy, genes can be present in three copies "trisomy" or in only one copy "monosomy". These changes in chromosome number, resulting from nondisjunction of chromosomes during meiosis, have dramatic effects on the affected persons and result in well-known syndromes. The majority of trisomies and monosomies are lethal to the fetus and cause spontaneous abortions or death immediately after birth. Some aneuploidies, however, are viable and result in syndromes. The most occurring aneuploidies among live births are chromosomes 21, 18, 13 trisomy's and a distorted number of sex chromosomes. The most common autosomal aneuploidy that infants can survive with is trisomy 21 (Down syndrome), affecting 1 in 800 births. Trisomy 18 (Edwards syndrome) affects 1 in 6,000 births, and trisomy 13 (Patau syndrome) affects 1 in 10,000 births. Sex chromosome aneuploidy (SCA) affects 1 in 400 newborns and is therefore, as a whole, more common than Down syndrome. While SCA include a variety of abnormalities of the sex chromosomes, by far the most commonly occurring SCA is the deletion of chromosome X (45,X-Turner syndrome) or the addition of an X or Y chromosome (47,XXY-Klinefelter syndrome, 47,XYY, 47,XXX). Of these conditions, only Turner syndrome results in an easily identifiable physical phenotype. However, subtle language and learning difficulties have been identified in most forms of SCA. The most important risk factor for aneuploidy is maternal age since the majority of children with aneuploidy are born to mothers over the age of 35, so the prevalence is increasing as more women choose or need to delay childbearing. Contemporary prenatal screening programs typically include the common fetal chromosomal aneuploidies 21, 18 and 13. The risk of a pregnancy is assessed by a number of means. For the chromosomal aneuploidies non-invasive screening tests based on ultrasonography and the measurement of markers in maternal serum have been implemented to identify high-risk pregnancies in the first 3 months of pregnancy (11-14 weeks). The sonogram measures the fluid underneath the skin along the back of the baby's neck, called the nuchal translucency (NT). The sonogram will also determine if the baby's nasal bone is present or absent. A maternal blood sample is used to analyze two serum markers called free beta-human chorionic gonadotropin (hCG) and pregnancy associated plasma protein-A (PAPP-A), which are found in the blood of all pregnant women. In aneuploidy pregnancies there is extra fluid behind the baby's neck and/or the hCG and PAPP-A results are higher or lower than average. Additionally, a baby's nasal bone may be absent in some pregnancies with a chromosome abnormality. Combining age-related risk with the NT measurement, nasal bone data, and blood markers provide a risk figure for Down syndrome and one risk figure for trisomy 13 or trisomy 18. The first trimester screen's detection rate is approximately 90% with a 5% false positive rate for pregnancies in which the baby has Down syndrome, and is somewhat higher for pregnancies with trisomy 13 or trisomy 18. A nuchal translucency sonogram can be performed without measuring hCG and PAPP-A. In this case, however, the aneuploidy detection rate is reduced to about 70%.

Prenatal diagnosis is an integral part of obstetric practice. To perform a genetic diagnosis prenatally, genetic material from the unborn fetus is required. Conventionally, fetal DNA is sampled by invasive procedures such as amniocentesis or chorionic villus sampling. These procedures are associated with a risk of miscarriage of respectively 0.5 and 1-2%. Hence, it is routine to reserve the invasive diagnostic procedures for pregnancies estimated to be at high aneuploidy risk which represent about 5-10% of all women screened for aneuploidy risk. Given the procedure related risks of conventional prenatal diagnosis, it would be ideal if genetic analysis of the fetus could be performed non-invasively. To perform non-invasive prenatal diagnosis, a source of fetal genetic material without harming the fetus is therefore required. A major breakthrough to this end was reported by Lo et al. (1997)[1] and WO98/39474 describing the existence of free floating fetal DNA in maternal plasma. They subsequently showed that fetal-derived DNA contributed ~10% of the free-floating DNA in maternal plasma. Fetal DNA can be detected in maternal plasma just weeks after conception and is rapidly cleared from maternal plasma and disappears within hours after delivery. As a result, free floating fetal DNA in maternal plasma is a promising source of fetal genetic material for the development of a non-invasive prenatal test. However, fetal DNA represents only a minor fraction of the total free floating DNA in plasma with the remaining portion of DNA contributed by the mother, mainly derived from maternal white blood cells.

Given the enormous potential, several non-invasive methodologies for aneuploidy detection have been described in the last decade. One method is to focus on the analysis of nucleic acid molecules that are fetal-specific in maternal plasma and hence overcome the interference caused by the background maternal DNA. One could target the detection of placental expressed mRNA or placenta-specific epigenetic signatures originating from the chromosome of interest. In a series of developments since 2000, the basis for plasma RNA as a prenatal diagnostic tool has been established. Poon et al. (2000)[2] showed that mRNA transcribed from the Y chromosome could be detected in the plasma of women carrying male fetuses. Later, it was shown that the placenta is a major source of fetal-derived RNA in maternal plasma using human placental lactogen mRNA and mRNA coding for the beta subunit of human chorionic gonadotrophin as examples[3].

In 2007, a placental-specific mRNA, transcribed from a gene located on chromosome 21, PLAC4, was identified using a microarray-based approach and was shown to be detectable in maternal plasma and cleared following delivery of the fetus[4]. To determine the dosage of chromosome 21 using PLAC4 mRNA in maternal plasma the RNA-SNP allelic ratio approach was used. This method is based on the presence of a SNP in the coding region of the PLAC4 gene. If a fetus is heterozygous for this SNP, it possesses two alleles that are distinguishable by DNA sequence. If the fetus is euploid, the ratio of these two SNP alleles is 1:1. Conversely, if the fetus has trisomy 21, then the RNA-SNP allelic ratio would become 1:2 or 2:1. Lo et al. (2007)[4] demonstrated that this strategy could be applied to non-invasively determine the chromosome 21 trisomy status of a fetus. Similarly, the RNA-SNP approach was also applied for the non-invasive detection of trisomy 18 through the analysis of the allelic ratio of SERPINB2 mRNA[5].

The main limitation of the RNA-SNP allelic ratio approach, however, is that only fetuses heterozygous for the analyzed SNP can be successfully diagnosed. For example, with the use of the single SNP in PLAC4, approximately 45% of fetuses are expected to be heterozygous and thus diagnosable using this approach. Consequently, several markers are needed for full diagnostic coverage. To this end, a number of investigators have described new polymorphic SNP markers that can be analyzed using this approach. One preliminary report describes ten markers with a combined heterozygosity rate that covers up to 95% of the US general population[6]. The evaluation of these markers in large-scale clinical trials is expected over the next few years.

Placenta-specific epigenetic signatures, such as DNA methylation, originating from the fetal chromosome of interest have also been investigated. As tissues in the body have different gene expression profiles, the methylation status of certain genes also exhibits tissue-specific patterns. Evidence shows that fetal DNA in maternal plasma originates from the placenta and that the maternal DNA background is derived from maternal blood cells. Therefore, one way to develop epigenetic fetal DNA markers is to identify genes whose methylation status differs between placental tissues and maternal blood cells. Chim et al. (2005)[7] studied the methylation profile of the SERPINB5 (maspin) promoter and showed that it was hypomethylated in placental tissues but hypermethylated in maternal blood cells. Using methylation specific PCR, the placental-derived hypomethylated SERPINB5 could be detected and distinguished from the maternally derived hypermethylated molecules in maternal plasma. This made SERPINB5, located on chromosome 18, the first universal circulating fetal DNA marker that could be used for all pregnancies regardless of fetal gender and genotype. Since the SERPINB5 gene is located on chromosome 18, it allowed the development of a strategy that is analogous to the RNA-SNP allelic ratio approach, the so-called epigenetic allelic ratio approach. Thus, if a fetus is heterozygous for an SNP located in the promoter region of SERPINB5, measuring the ratio of the SNP alleles in the hypomethylated version of the gene, allows ascertainment of the fetus's trisomy 18 status.

However, methylation-specific PCR requires the use of a bisulphite conversion, which alters unmethylated cytosines to uracil nucleotides. But, bisulphite conversion degrades up to 95% of the DNA molecules in a sample and therefore substantially reduces the amount of fetal DNA in a maternal plasma sample and may result in false-negative detection. Consequently, researchers developed fetal epigenetic markers that could be detected in maternal plasma without the need for bisulphite conversion. To this end, Chan et al. (2006)[8] used the promoter of RASSF1, located on chromosome 3, which is hypermethylated in placental tissues but hypomethylated in maternal blood cells. Consequently, the hypomethylated RASSF1 sequences derived from the maternal blood cells can be removed from maternal plasma using methylation sensitive restriction enzyme digestion. Indeed, after restriction enzyme digestion, fetal RASSF1 sequences could be detected in maternal plasma before delivery but completely disappeared from maternal plasma within 24 h after delivery. Chan et al. (2006)[9] used the differential methylation pattern of the RASSF1 promoter as the positive control for fetal DNA detection in a non-invasive prenatal fetal rhesus D blood group typing for 54 early-gestation RhD-negative women.

The RNA-SNP allelic ratio approach and the DNA methylation approach target subsets of nucleic acid molecules present in maternal plasma in a molecular fashion. An alternative is using physical methods that result in the relative enrichment of fetal DNA present in the maternal plasma.

Recently[9], it was shown that the length of free floating fetal DNA in the maternal plasma is ~20 bp shorter than the maternally derived free-floating DNA. Therefore, size fractioning methods such as gel electrophoresis allow size-fractionation of plasma DNA and enrichment of the shorter, fetal DNA fragments. This approach has been used successfully to enrich for free floating fetal DNA. While this approach has been shown empirically to be useful for the qualitative detection of disease causing mutations, for example those causing beta-thalassemia, it is yet unknown whether the degree of enrichment might be sufficient for fetal chromosomal aneuploidy detection requiring quantitative measurement of chromosome dosage. Dhallan et al. (2006)[10] reported another approach for the enrichment of fetal DNA in maternal plasma. They hypothesized that a significant portion of maternal derived free-floating DNA in maternal plasma is released by maternal white blood cells following phlebotomy. Therefore it was proposed that if maternal nucleated blood cells could be fixed, using formaldehyde, then this dilution of fetal DNA in maternal plasma could be avoided. Dhallan[10] demonstrated the benefit of this approach for the noninvasive prenatal diagnosis of trisomy 21 showing a mean proportion fetal DNA of 34% in an experiment comprising 60 pregnant women. However, the beneficial effects of formaldehyde treatment could not be replicated by several other groups.

The above-mentioned approaches are based on the assumption that the low fractional concentration of fetal DNA in maternal plasma makes it challenging to pursue the direct detection of fetal chromosomal aneuploidies. This is based on the limited precision of conventional methods for circulating fetal DNA detection, for example by real-time PCR.

The recent availability of single molecule counting techniques allows detection of fetal aneuploidy without the need to restrict the analysis to fetal-specific nucleic acids in maternal plasma. Digital PCR and massively parallel sequencing are both single molecule counting methods, which allow the quantification of nucleic acids by counting molecules and have superior analytical precision compared to conventional PCR based detection methods. Digital PCR refers to the performance of multiple PCRs in parallel in which each PCR typically contains either a single or no target molecule. Through the counting of the number of positive reactions at the end of amplification it is possible to determine the number of input target molecules. Thus, they can precisely quantify small increments in the total (maternal vs. fetal) amount of DNA molecules derived from the aneuploid chromosome. Indeed, Lo et al. (2007)[11] demonstrated that the aneuploidy status detection is possible even when the trisomic DNA is present as a minor (10%) fraction.

The lower the fetal DNA concentration, the smaller the expected increment in the amount of aneuploidy chromosome DNA. For digital PCR, quantitative precision improves with increasing number of PCR analyses performed. Lo et al. (2007)[11] showed that accurate fetal trisomy 21 detection in a maternal plasma sample containing 25% fetal DNA requires about 8000 digital PCRs to be performed, requiring the use of automated platforms in the clinical setting. Such automated platforms using microfluidics are available (e.g. Fluidigm) but are expensive. Several groups demonstrated that non-invasive detection of fetal trisomy 21 could be achieved with the use of massively parallel, or next-generation, sequencing (e.g. WO2009/013496). Massively parallel sequencers allow analysis of nucleotide sequences of millions to billions of DNA molecules in each run. Therefore, in addition to the identity, a frequency distribution of the DNA molecules in the analyzed sample can be obtained. Since free floating DNA in maternal plasma is fragmented in nature it can be used directly to identify the chromosomal origin of each DNA molecule and determine the proportion of molecules derived from a potentially aneuploid chromosome. Several groups showed that the proportion of chromosome 21 DNA molecules in plasma of women pregnant with a trisomy 21 fetus was elevated compared with that of euploid pregnancies. This approach was highly accurate for the direct detection of fetal trisomy 21 from maternal plasma among small cohorts of pregnancies.

Recently, two clinical validation studies were performed applying the above-described method. In one study 449 samples were analyzed of which 39 were trisomic for chromosome 21[12]. A second study analyzed blood samples from 1014 at risk pregnancies collected in 13 US clinic locations before they underwent an invasive prenatal procedure[13]. Of these 119 samples underwent massively parallel DNA sequencing. Fifty-three sequenced samples were classified correctly as having an abnormal fetal karyotype. Both clinical validation studies showed excellent sensitivity and specificity. These data demonstrate that plasma DNA sequencing is a viable method for noninvasive detection of fetal trisomy 21 and warrants clinical validation in larger multicenter study.

On the other hand, it has been shown that the measurement of the proportional amounts of sequences derived from chromosomes with higher or lower GC contents then chromosome 21 was not as robust. Therefore, the measurements for chromosomes 18 and 13 are less precise and suffer from quantitative bias using trisomy 21 protocols. Thus, to achieve reliable non-invasive detection of trisomy 18 and trisomy 13, sequencing and data analysis protocols that are less susceptible to the chromosomal GC content effects need to be developed and further validated. A recent study partially solved the above problem using a non-repeat masked reference genome and a bioinformatics approach to correct GC content bias in the sequencing data[14]. Using this approach all trisomy 13 fetuses (25 out of 25) were detected at a specificity of 98.9% and 92% (34 out of 37) of the trisomy 18 fetuses at 98.0% specificity. These data indicate that with appropriate bioinformatics analysis, noninvasive prenatal diagnosis of trisomy 13 and trisomy 18 by maternal plasma DNA sequencing is not as reliable as trisomy 21.

In addition, the cost of massively parallel sequencing is high and the throughput is low. Only a handful of cases can be analyzed per run, which takes several days. Further work is needed to develop more cost-effective protocols with higher throughput.

Recently, target enrichment was used to obtain a more efficient and cost-effective massive parallel sequencing approach[15]. This study investigated the applicability in enriching selected genomic regions from plasma DNA and the quantitative performance of this approach. The experiment showed that the mean sequence coverage of the enriched samples was ~200-fold higher than that of the non-enriched samples and more importantly that maternal and fetal DNA molecules were enriched evenly. Furthermore, by using SNP data the authors were able to show that the coverage of fetus-specific alleles within the targeted region increased from 3.5% to 95.9%. Overall, targeted sequencing of maternal plasma DNA allows efficient and unbiased detection of fetal alleles and is a powerful method for measuring the proportion of fetal DNA in a maternal plasma sample. Based on this single scientific paper target enrichment shows great promise since it can reduce the sequencing cost substantially. At the same time it requires an extra, enrichment step that will add an extra cost to the final test and also will delay the test since a typical enrichment protocol takes about 24-36 hours to complete.

SUMMARY OF THE INVENTION

The present invention provides a non-invasive diagnostic DNA test for aneuploidy detection of chromosomes 21 and/or 18 and/or 13 and/or X and/or Y by combining multiplex PCR based amplification of specific DNA sequences (i.e. targets) which contain at least one SNP in combination with sequencing technologies.

In another aspect the invention provides a non-invasive diagnostic DNA test for aneuploidy detection of chromosomes 21 and 18 and 13 and X and Y by combining multiplex PCR based amplification of specific DNA sequences (i.e. targets) which contain at least one SNP in combination with sequencing technologies.

Briefly, the present invention is directed to a method of differential detection of a predetermined set of target sequences in a mixture of maternal and fetal genetic material. Thus, the methods and materials described herein apply techniques for analyzing numerous nucleic acids contained in a biological sample (preferably serum or plasma) containing free floating DNA which is a mixture of DNA from both the mother and the fetus, and allowing detection of statistically significant difference between euploid and, triploid fetuses. In contrast to the current massive parallel sequence methods, based on whole genome or enriched samples, which do not achieve a sufficient sensitivity and specificity, in particular, for chromosome 13, the present invention provides a non-invasive diagnostic assay with a specificity and sensitivity close to 100% (respectively 99.99% specificity and 99.5% sensitivity) for the simultaneous detection of chromosome 13, 18, 21, X and Y aneuploidies. Without limiting the invention to a particular theory or explanation, one reason why multiplex-PCR was not considered before in the development of non-invasive diagnostic aneuploidy tests is the presence of high GC-rich regions particularly in chromosome 13. Yet another reason is that the use of multiplex-PCR was discouraged by one of the leading inventors (i.e. Dennis Lo) in US2010/0112590. Indeed, in the latter application on paragraphs 116-117 it is recommended to apply locus-independent assays rather than locus-dependent assays such as for example the targeted amplification carried out by the methods of the present invention.

Thus in one aspect the invention provides a method for determining the presence or absence of fetal aneuploidy in a biological sample comprising fetal and maternal nucleic acids present in free floating DNA from said maternal biological sample, amplifying a selected set of target DNA sequences in a quantitative (i.e. amplifying the template DNA such that the amplified DNA is reproducing the original template DNA ratios) multiplex PCR reaction, conducting DNA sequencing of said amplified selected set of target DNA sequences to determine the sequence of said DNA sequences, using the obtained sequence data to compare an amount of amplified sequences derived from at least one first chromosome in said mixture of maternal and fetal DNA to an amount of amplified DNA sequences derived from at least one second chromosome in said mixture of maternal and fetal DNA, wherein said at least one first chromosome is presumed to be euploid in the fetus, wherein said at least one second chromosome is suspected to be aneuploid in the fetus, thereby determining the presence or absence of said fetal aneuploidy.

In another aspect the invention provides a method for determining the presence or absence of fetal aneuploidy in a biological sample comprising fetal and maternal nucleic acids (such as free floating DNA) from said maternal biological sample, amplifying a selected set of target DNA sequences in a quantitative multiplex PCR reaction wherein each amplified DNA sequence comprises at least one SNP which is considered informative in case the pregnant female is heterozygous for this SNP, conducting DNA sequencing of said amplified selected set of target DNA sequences to determine the sequence of said DNA sequences, using the obtained sequence data to compare an amount of amplified sequences which carry an informative SNP derived from at least one first chromosome in said mixture of maternal and fetal derived DNA to an amount of amplified DNA sequences which carry an informative SNP derived from at least one second chromosome in said mixture of maternal and fetal derived DNA, wherein said at least one first chromosome is presumed to be euploid in the fetus, wherein said at least one second chromosome is suspected to be aneuploid in the fetus, thereby determining the presence or absence of said fetal aneuploidy and/or determining in said determined DNA sequences the allelic ratios of the informative SNPs wherein a distorted allelic ration is indicative for the presence of a fetal chromosomal aneuploidy in said pregnant female.

FIGURE LEGENDS

FIG. 1:

Dosage Quotients (DQ) of trisomic fetus when compared to euploid fetus. The grey shaded area indicates the expected percentages of fetal DNA.

FIG. 2:

Number of SNPs needed to gent minimally a given number of informative SNPs, plotted per Minor Allele Frequency (MAF). The calculations are done for a minimal probability of 99%.

Figure 3:
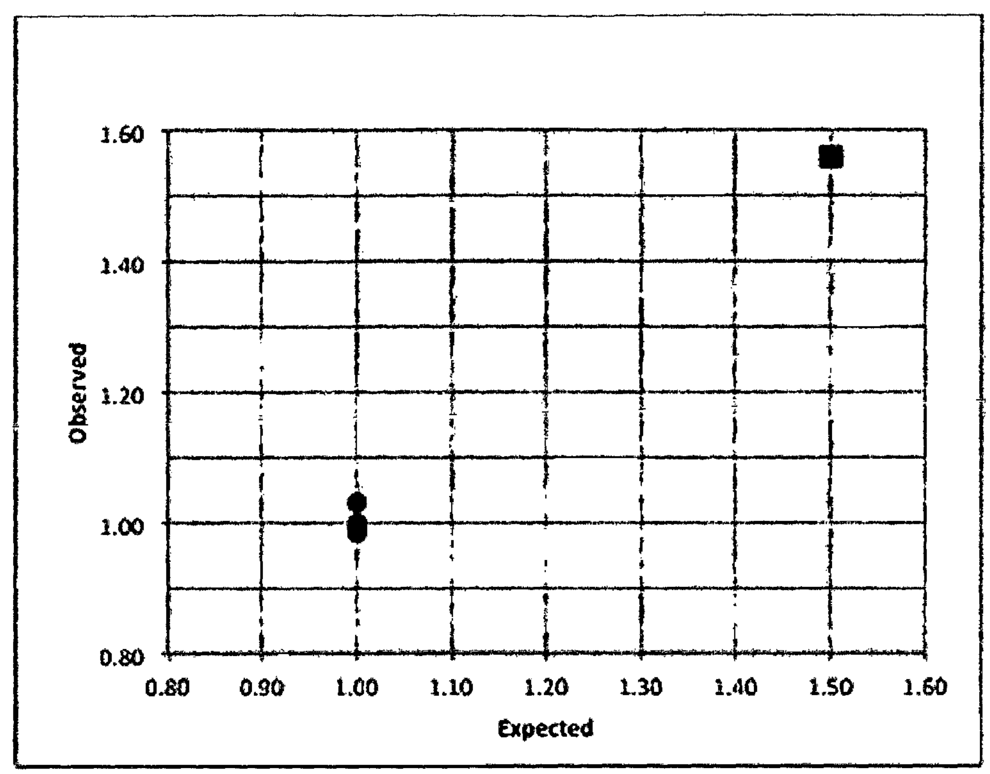

FIG. 3: plot of expected vs. observed normalized read counts for chromosome 21 in a Down syndrome (trisomy 21) DNA samples (square) and 4 euploid DNA samples (circles).

Figure 4:
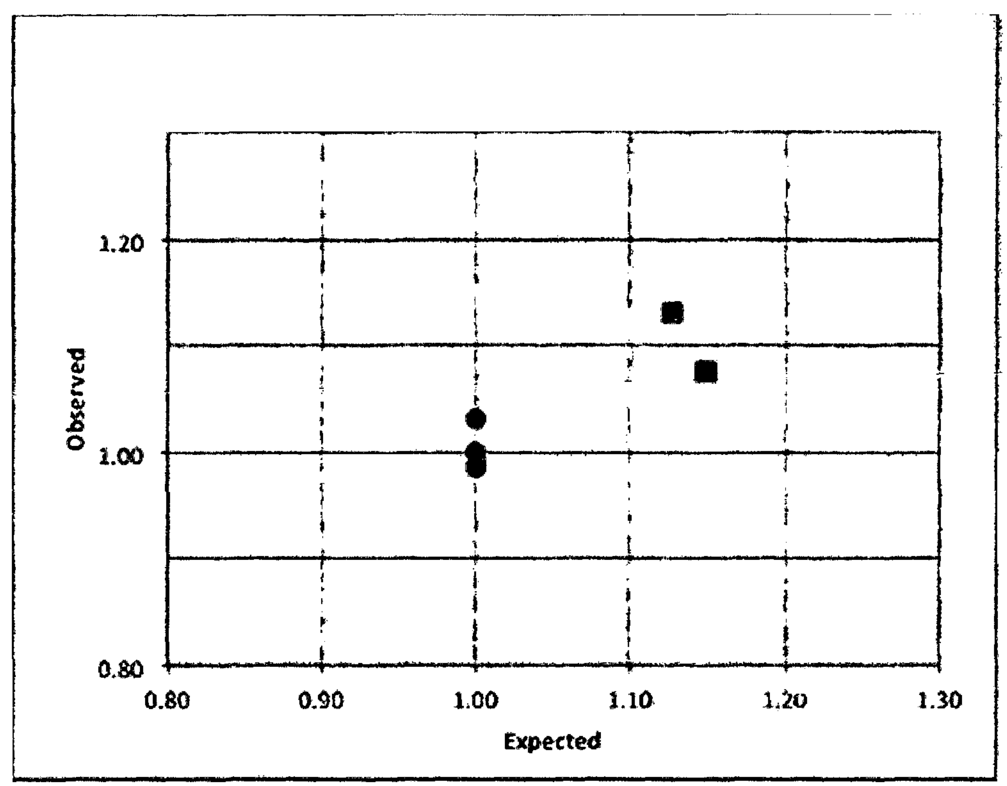

FIG. 4: plot of expected vs. observed normalized read counts for two ATP samples (representing 20% trisomy 21) DNA samples (squares) and 4 euploid DNA samples (circles).

Figure 5:
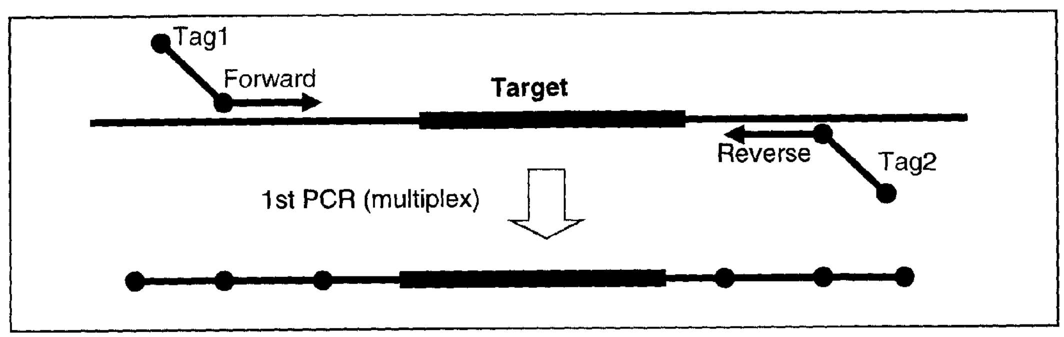
Figure 6:
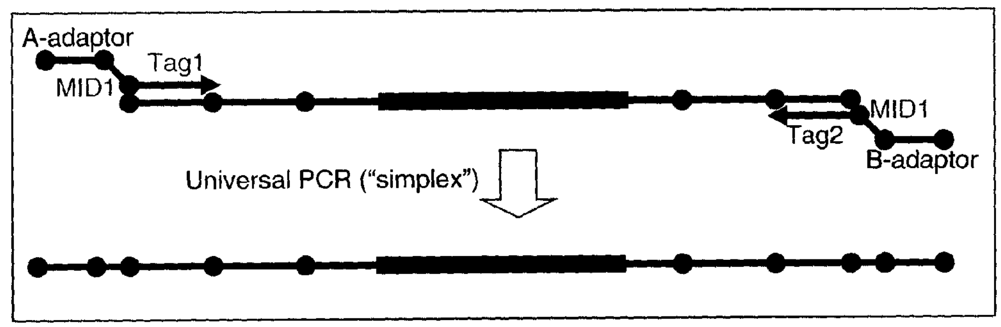

FIG. 5: schematic representation of first multiplex PCR reaction of the MASTR assays procedure. Reverse and forward primers are amplicon specific primers. Tag1 and Tag2 are universal sequencing that are used in the second PCR reaction of the MASTR assay procedure to incorporate FIG. 6: schematic representation of the second PCR reaction of the MASTR procedure. In this step the MID sequences (barcodes) and A and B adaptors (for 454 emulsion PCR) are incorporated in the resulting amplicons from the first PCR reaction.

DETAILED DESCRIPTION OF THE INVENTION

The prior art has shown the feasibility of massive parallel sequencing as an analysis platform for free floating DNA based aneuploidy testing. However, current protocols result in expensive and low throughput tests when used as a molecular diagnostic tool. The main reason for this is the fact that current tests are based on genome wide sequencing of free floating DNA resulting in the production of huge sequencing datasets of which only a small fraction (~5%) is used to determine the ploidy status of the fetus. With this genome wide approach it is obligatory to use a substantial part of the capacity of a massive parallel sequencer resulting in sequencing of a limited number of individuals per run, which takes several days to complete. Furthermore, huge sequencing datasets are generated per individual that hamper efficient data storage and analysis.

The present invention offers a solution for this problem by using a multiplex-PCR based approach to amplify a number of selected chromosomal regions. Selected chromosomal regions are amplified in a multiplex PCR reaction from one or more chromosomes which are presumed to be aneuploid and selected set of chromosomal regions are amplified, preferably in the same multiplex PCR reaction, from one or more chromosomes which are presumed to be euploid. Chromosomes which are presumed to be euploid are herein further designated as a 'reference chromosome'.

Accordingly the present invention provides in a first embodiment a method for the detection of a fetal chromosomal aneuploidy in a pregnant female comprising i) receiving a biological sample from said pregnant female, ii) preparing nucleic acids from said biological sample, iii) amplifying a selected set of target DNA sequences in a quantitative multiplex PCR reaction wherein at least one amplified DNA sequence comprises at least one SNP which is considered informative if the pregnant female is heterozygous for this SNP, iv) sequencing of the amplified target DNA sequences and v) calculating the sum of read counts for all amplified DNA sequences of a suspected chromosomal aneuploidy followed by normalization, against the sum of read counts for all amplified DNA sequences of a reference chromosome to determine by statistical methods a set score indicative for the presence of a fetal chromsomal aneuploidy and/or determining the allelic ratios of the informative SNPs wherein a distorted allelic ratio is indicative for the presence of a fetal chromosomal aneuploidy in said pregnant female.

The term "biological sample" as used herein refers to any sample that is taken from a subject (e.g. such as a pregnant female or a pregnant woman) and contains one or more nucleic acid molecule(s) of interest.

Accordingly a biological sample comprises for example blood, sputum, urine, cerebrospinal fluid (CSF), tears, plasma, serum, saliva or transcervical lavage fluid.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues The term nucleic acid is used interchangeably with gene, cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain. It may include regions preceding and following the coding region (leader and trailer) as well as intervening sequences (introns) between individual coding segments (exons). The term "reaction" as used herein refers to any process involving a chemical, enzymatic, or physical action that is indicative of the presence or absence of a particular polynucleotide sequence of interest. An example of a "reaction" is an amplification reaction such as a polymerase chain reaction (PCR), preferably a multiplex PCR reaction. Another example of a "reaction" is a sequencing reaction, either by synthesis or by ligation. The term "clinically relevant nucleic acid sequence" as used herein can refer to a polynucleotide sequence corresponding to a segment of a larger genomic sequence whose potential imbalance is being tested or to the larger genomic sequence itself. Examples include chromosome 18, 13, 21, X and Y. Yet other examples include mutated genetic sequences or genetic polymorphisms or copy number variations that a fetus may inherit from one or both of its parents. The term "background nucleic acid sequence" as used herein may refer to nucleic acid sequences originating from the mother or originating from the chromosome not tested for aneuploidy in a particular analysis.

The term "free-floating DNA" is DNA which is derived from genomic DNA, free-floating DNA is in fact degraded genomic DNA and occurs in the extra-cellular space. As such free-floating DNA can be isolated from body fluids (e.g. serum, plasma, sputum). The term "quantitative data" as used herein means data that are obtained from one or more reactions and that provide one or more numerical values. The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "cutoff value" as used herein means a numerical value whose value is used to arbitrate between two or more states (e.g. diseased and non-diseased) of classification for a biological sample. For example, if a parameter is greater than the cutoff value, a first classification of the quantitative data is made (e.g. diseased state); or if the parameter is less than the cutoff value, a different classification of the quantitative data is made (e.g. non-diseased state).

The term "imbalance" as used herein means any significant deviation as defined by at least one cutoff value in a quantity of the clinically relevant nucleic acid sequence from a reference quantity.

The term "chromosomal aneuploidy" as used herein means a variation in the quantitative amount of a chromosome from that of a diploid genome. The variation may be a gain or a loss. It may involve the whole of one chromosome or a region of a chromosome. Examples of chromosomal aneuploidies are derived from chromosome 13, 18, 21, X and Y.

The term "random sequencing" as used herein refers to sequencing whereby the nucleic acid fragments sequenced have not been specifically identified or targeted before the sequencing procedure. Sequence-specific primers to target specific gene loci are not required when random sequencing is applied. The pools of nucleic acids sequenced vary from sample to sample and even from analysis to analysis for the same sample. In random sequencing the identities of the sequenced nucleic acids are only revealed from the sequencing output generated in contrast to sequencing of multiplex PCR amplified nucleotide sequences.

Embodiments of this invention provide methods, systems, and apparatus for determining whether an increase or decrease (diseased state) of a clinically-relevant chromosomal region exists compared to a non-diseased state. This determination may be done by using a parameter of an amount of a clinically-relevant chromosomal region in relation to other non-clinically-relevant chromosomal regions (background regions) within a biological sample. Nucleic acid molecules of the biological sample are sequenced, such that a fraction of the genome is sequenced, and the amount may be determined from results of the sequencing. One or more cutoff values are chosen for determining whether a change compared to a reference quantity exists (i.e. an imbalance), for example, with regards to the ratio of amounts of two chromosomal regions (or sets of regions).

The change detected in the reference quantity may be any deviation (upwards or downwards) in the relation of the clinically-relevant nucleic acid sequence to the other non-clinically-relevant sequences. Thus, the reference state may be any ratio or other quantity (e.g. other than a 1-1 correspondence), and a measured state signifying a change may be any ratio or other quantity that differs from the reference quantity as determined by the one or more cutoff values.

The clinically relevant chromosomal region (also called a clinically relevant nucleic acid sequence or suspected aneuploid chromosome or chromosomal region) and the background nucleic acid sequence may come from a first type of cells and from one or more second types of cells. For example, fetal nucleic acid sequences originating from fetal/placental cells are present in a biological sample, such as maternal plasma, which contains a background of maternal nucleic acid sequences originating from maternal cells. Preferentially, maternal and fetal nucleic acid sequences are derived from free-floating DNA. In one embodiment, the cutoff value is determined based at least in part on a percentage of the first type of cells in a biological sample. Note the percentage of fetal sequences in a sample may be determined by any fetal-derived loci and not limited to measuring the clinically-relevant nucleic acid sequences.

In another embodiment the methods of the invention use cell (e.g. blood cells) stabilizing chemicals in the preparation of the nucleic acids present in the biological sample which is received from the pregnant female. Indeed, one of the major technical challenges in using free-floating fetal DNA from maternal blood is the low fraction of fetal DNA present in the sample. This fraction is typically between 10 and 20% in the first trimester of pregnancy (week 11-14), which corresponds with the stage where an aneuploidy DNA test is best performed. This low fraction of fetal DNA is even for molecular counting methods challenging with respect to the sensitivity and specificity of the test. Therefore it is important to maximize the ratio fetal/maternal free floating DNA. The present invention provides different solutions for this problem.

In a particular embodiment the disruption of nucleated blood cells is prevented during the collection, storage or transport of the biological material, in particular a maternal blood sample prior to plasma isolation. This is important to prevent dilution of fetal DNA resulting in a decreased ratio fetal/maternal free floating DNA. Several commercial cell stabilizing blood collection tubes are available which stabilize blood cells for at least 14 days at room temperature allowing convenient sample collection, transport and storage (available for example at www.streck.com).

In yet another particular embodiment a size fractionation is used in the methods of the invention to prepare maternal and fetal nucleic acids.

Indeed, the prior art shows that fetal and maternal free-floating DNA have different size distributions. Free floating fetal DNA is generally 20 bp shorter than the maternal free floating DNA and this observation can be used to further enrich the free-floating fetal DNA fraction if this smaller sized fraction is specifically separated from the maternal fraction. One way to accomplish this is by means of gel electrophoresis. In a particular embodiment, a gel electrophoresis based size-fractionating device is used as marketed by Sage Science (www.sagescience.com). This device is a fully automated system enabling tight size selection and a high recovery rate. Furthermore, it eliminates the cross contamination risk completely since all samples are separated from each other during the whole size fractionation process.

In a particular embodiment the amplified DNA sequences obtained in the quantitative multiplex PCR reaction in the methods of the invention have a size between 80 and 140 base pairs.

In view of the size distributions of the fetal and maternal free floating DNA populations it is essential to keep the amplified DNA sequence lengths below 140 bp to ensure efficient amplification of the shorter fetal free-floating DNA fraction.

Preferred amplified DNA sequence lengths are between 80 and 140 basepairs.

In yet another embodiment the amplified DNA sequences obtained in one single multiplex PCR reaction are between 30 and 60.

In yet another embodiment the amplified DNA sequences obtained in one single multiplex PCR reaction are between 60 and 80.

In yet another embodiment the amplified DNA sequences obtained in one single multiplex PCR reaction are between 70 and 80.

Preferably only one quantitative multiplex RCR reaction is applied to practice the methods of the invention.

In yet another embodiment the GC-content of the target DNA sequences (i.e. the DNA sequences which are amplified with the quantitative multiplex PCR reaction) is between 30% and 70%. Our experimental data point out that a range of 40%-60% GC is optimal for a close to 100% sensitivity and specificity of the methods of the invention.

An essential step in the methods of the present invention is the sequencing of the amplified target DNA sequences. As a high number of sequencing reads, in the order of hundred thousand to millions or even possibly hundreds of millions or billions can theoretically be generated from each sample in each run, the resultant sequenced reads form a representative profile of the mix of nucleic acid species in the original biological sample. However, the person skilled in the art would know how many runs to perform based on the stage of pregnancy (which is correlated with the amount of free-floating fetal DNA in the biological sample) and based on the origin of the biological sample derived from a pregnant female. The most important aspect is that a high degree of statistical confidence is obtained. In order to improve statistical confidence, it is preferable to perform a large number of reads, preferably between 10.000 and 100.000 or more reads, depending on the percentage of fetal DNA present in the mixture. A commonly used measure of statistical significance when a highly significant result is desired is $p<0.01$, i.e. a 99% confidence interval based on a chi-square or t-test.

In a preferred embodiment massive parallel sequencing methods are used. In particular embodiments, the sequencing is done using massively parallel sequencing. Massively parallel sequencing, such as for example on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001), allow the sequencing of many nucleic acid molecules isolated from a specimen at high orders of multiplexing in a parallel fashion. Each of these platforms sequences clonally expanded or even non-amplified single molecules of nucleic acid fragments.

An important advantage of the limited set of amplified nucleotide sequences which is generated by the methods of the present invention is that emerging low cost and lower capacity massive parallel sequencers can be used such as the 454 junior (Roche), PGM (Life Technologies) or MiSeq (Illumina). The combination of the methods of the invention and the low end sequencers results in a fast turnaround time per test since these platforms typically take only a few hours per sequencing run. In addition, the lower cost is also an important improvement over the methods used in the prior art.

In a particular embodiment the massive parallel sequencing data are analyzed by calculating the sum of read counts for all amplified DNA sequences of a suspected chromosomal aneuploidy (e.g. all amplified DNA sequences derived from chromosome 21 and/or chromosome 13 and/or chromosome 18 and/or chromosome X and/or chromosome Y) are counted (i.e. the number of times a specific amplified chromosomal sequence is present in the biological sample). The sum of read counts for the amplified DNA sequences derived from a particular suspected aneuploid chromosome (e.g. chromosome 13 or 18 or 21 or X or Y) is then normalized against the sum of read counts for the amplified DNA sequences derived from a reference chromosome (i.e. a chromosome for which no aneuploidy is reported). Thus, the multiplex PCR allows the calculation of dosage quotients (DQs) by comparing (target region read count, i.e. the suspected aneuploidy chromosome or chromosomal region)/(control region read count, i.e. the reference chromosome or chromosomal region) ratios between the pregnant female and the fetus. The DQs in function of the percentage fetal DNA is depicted in FIG. 1.

An essential element of the methods of the present invention is that the amplified target DNA sequences are reflecting identical ratios of the amounts of maternal and fetal free floating nucleic acids in the biological sample and hence the methods require quantitative amplification. Based on multiplex PCR assays and the PCR conditions used to amplify samples (limited number of cycles) we previously showed that template DNA is amplified quantitatively. If there is a normal distribution between the two read counts then a score (e.g. a Z-score or a dosage quotient) is obtained. A Z-score of 1 means that there is no aneuploidy for the suspected aneuploidy chromosome. A Z-score higher than 1, preferentially higher than 2, more preferentially higher than 3, is an indication for the presence of an aneuploidy of the chromosome. It is understood that Z-scores are determined for all the suspected aneuploidy chromosomes for which a selected set of target DNA sequences are obtained by the methods of the invention. The normalization and the calculation of the Z-score is assisted by the use of statistical methods. Useful statistical methods which can be used in the context of the present invention include Bayesian-type likelihood method, sequential probability ratio testing (SPAT), false discovery, confidence interval and receiver operating characteristic (ROC).

Figure 2:
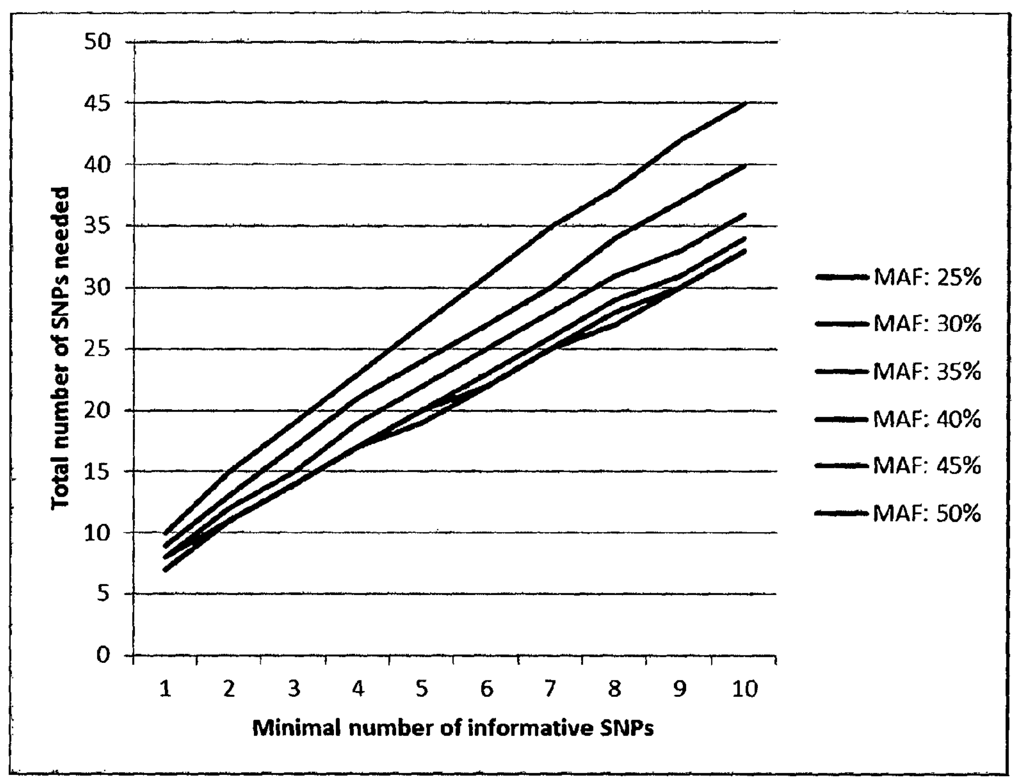

In yet another particular embodiment the massive parallel sequencing data of the amplified target DNA sequences are analyzed based on the determination of the allelic ratios of the informative SNPs wherein a distorted ratio is indicative for the presence of a fetal chromosomal aneuploidy in the pregnant female. The allelic ratio is distorted for informative SNPs on aneuploid chromosomes. This distortion can be measured when the mother is heterozygous for a given SNP (referred herein as "informative SNP"). Therefore, sequence analysis of the MASTR assay will result in a number of informative SNPs that can be used to determine the fetal ploidy status on top of the fetal ploidy status determination by molecular counting as described above. FIG. 2 shows the result of a calculation of the number of informative SNPs with a 99% probability provided a minor allele frequency (MAF) between 0.25 and 0.50. Based on this calculation it is depicted in FIG. 2 that with a minimal MAF of 0.25 at least 7 informative SNPs are present in a set of 35 amplified target DNA sequences, while 10 informative SNPs are identified for SNPs with a MAF of 0.50.

In yet another particular embodiment the massive parallel sequencing data of the amplified target DNA sequences are analyzed based on the determination of the allelic ratios of the informative SNPs wherein a distorted ratio is indicative for the presence of a fetal chromosomal aneuploidy in the pregnant female in combination with calculating the sum of read counts for all amplified DNA sequences of a suspected chromosomal aneuploidy (e.g. all amplified DNA sequences derived from chromosome 21 and/or chromosome 13 and/or chromosome 18 and/or chromosome X and/or chromosome Y) are counted (i.e. the number of times a specific amplified chromosomal sequence is present in the biological sample).

In yet another embodiment based on carrying out the methods of the invention a classification of whether a fetal chromosomal aneuploidy exists for one or more suspected aneuploid chromosomes determined. In one embodiment, the classification is a definitive yes or no. In yet another embodiment, a classification may be unclassifiable or uncertain. In yet another embodiment, the classification may be a score that is to be interpreted at a later date, for example, by a medical doctor.

In particular embodiments the bioinformatics, computational and statistical approaches used to determine if a biological sample obtained from a pregnant woman conceived with an aneuploid chromosome or chromosomal region or euploid fetus could be compiled into a computer program product used to determine parameters from the sequencing output. The operation of the computer program would involve the determining of a quantitative amount from the potentially aneuploid chromosome as well as amount(s) from one or more of the other chromosomes. A parameter would be determined and compared with appropriate cut-off values to determine if a fetal chromosomal aneuploidy exists for the potentially aneuploid chromosome.

In yet another embodiment the invention provides a diagnostic kit for carrying out the method of the invention. Such a diagnostic kit comprises at least a set of primers to amplify target maternal and target fetal nucleic acids wherein these target nucleic acids are derived from chromosome 13 and/or chromosome 18 and/or chromosome 21 and/or chromosome X and/or chromosome Y. Preferentially the kit comprises primers for amplifying target nucleic acids derived from chromosomes 13, 18, 21, X and Y. In addition, the diagnostic kit comprises a set of primers which are able to identify target DNA sequences of a reference chromosome or a reference chromosomal part. It is understood that such a reference chromosome or part thereof is an euploid chromosome. Euploid refers to the normal number of chromosomes. Other reagents which can optionally be included in the diagnostic kit are instructions and a polymerase and buffers to carry out the quantitative polymerase multiplex PCR reaction.

EXAMPLES

The following examples are offered to illustrate, but not to limit the claimed invention.

1. Prenatal Diagnosis of Fetal Trisomy 21

The DNA samples used in the present examples are samples prepared by mixing a diploid DNA sample derived from a female (representing the maternal DNA) with either a male DNA sample sample euploid for chromosome 21 (referred to as artificial euploid pregnancy or AEP) or with a male DNA sample triploid for chromosome 21 (referred to as artificial trisomy pregnancy or ATP). Each artificial sample was comprised of a mixture of 80% maternal DNA and 20% of male DNA. In addition, included in the analysis was a DNA sample derived from a Down syndrome individual, having 3 copies of chromosome 21.

Measurements were performed on 4 AEP samples, 2 ATP samples and 1 Down syndrome DNA sample. For each measurement, approximately 50 ng of DNA was used in a standard 2-step MASTR assay PCR amplification procedure (see Materials and Methods). The fetal chromosome 21 MASTR assay is comprised of 20 primer pairs derived from chromosome 21 and 10 primer pairs derived from chromosome 18. The resulting amplicons from each MASTR amplified individual DNA sample contained a specific barcode. The resulting barcoded amplicons of each DNA sample were equimolarly mixed and subjected to the 454 junior emulsion PCR protocol as described by the manufacturer. After emulsion PCR, beads were isolated and loaded on a 454 junior according to the manufacturer's protocol. A total of two 454 junior runs were performed in order to obtain sufficient reads to reach a per amplicon coverage between 300 and 500.

Since the Down syndrome DNA sample contains 3 chromosome 21 copies, it should provide 50% more chromosome 21 reads then the AEP samples. To calculate this, the following calculation steps were performed on the Down sample and on the AEP samples:

(i) Read counts for each chromosome 18 and 21 amplicon was divided by the total number of chromosome 18 derived read counts (ii) For each chromosome 18 and 21 amplicon, the average read count over the different AEP samples was calculated (iii) For each chromosome 18 and 21 amplicon, (i) was divided by (ii)

(iv) For each chromosome and each sample, the average value of (iii) was calculated (v) The observed normalized ratio chromosome21/chromosome18 was calculated by dividing averages calculated under (iv) per AEP and ATP FIG. 3 shows a plot of the observed (calculated as above) and expected (i.e. theoretical values) number of read counts for chromosome 21 amplicons of the Down DNA sample.

These data show that a clear distinction can be made between a normal, euploid DNA sample and a trisomy (i.e. Down syndrome), chromosome 21 DNA sample.

To evaluate the feasibility to distinguish between an euploid sample (represented by the AEP artificial samples) and an artificial chromosome 21 aneuploidy sample containing 20% chromosome 21 trisomy derived DNA, the above calculations were performed on the ATP samples relative to the AEP samples.

A presence of 20% of trisomy DNA in the ATP samples should result in a 10% increase in chromosome 21 amplicon read count compared to the AEP samples. Indeed using the above calculations, FIG. 4 shows a clear distinction between the AEP and ATP samples reflecting an approximately 10% increase in chromosome 21 in the two ATP samples.

Material and Methods

1. Primer Sequences Used in the Examples

TABLE 1 list of 30 primer pairs composing the chromosome 21 aneuploidy detection MASTR assay

| Amplicon | ChromForw | Rev |
|---|---|---|
| NITT_089 | chr18AAGACTCGGCAGCATCTCCATTTGGAGTTAGCTTGACTTTGG | GCGATCGTCACTGTTCTCCAGAGATGGTATTAGGAAGGTTTGGT |
| NITT_092 | chr18AAGACTCGGCAGCATCTCCACACTTTCTCCTAACACCCTTGG | GCGATCGTCACTGTTCTCCAGTGGGTGTCCTTAGGGGTCT |
| NITT_096 | chr18AAGACTCGGCAGCATCTCCATCAGCACTCCCTCCATGA | GCGATCGTCACTGTTCTCCACTCAAAGAAATGGAAGAGAATACA AAA |
| NITT_097 | chr18AAGACTCGGCAGCATCTCCACCTGCATCTTGACACAGTCG | GCGATCGTCACTGTTCTCCAGGCATCCAGGAGGAGAAAA |
| NITT_093 | chr18AAGACTCGGCAGCATCTCCAGGATGGTCACAGTGGGTCA | GCGATCGTCACTGTTCTCCAGAAGAGGGGAGAAGTAGAGGTTAA A |
| NITT_085 | chr18AAGACTCGGCAGCATCTCCATAAGCAAACAGCAGCACAAAA | GCGATCGTCACTGTTCTCCAGAGGGAATCTGTAATCCACATGA |
| NITT_094 | chr18AAGACTCGGCAGCATCTCCACCAGAGTGGAATTGCTGAGAC | GCGATCGTCACTGTTCTCCACTCCTTCTCTTCTTCTTCTTCTAA GC |
| NITT_084 | chr18AAGACTCGGCAGCATCTCCATGCAGATGGAGGACATCGT | GCGATCGTCACTGTTCTCCATTAAATTTGCTCTTGGTATACTTC TTG |
| NITT_083 | chr18AAGACTCGGCAGCATCTCCATGGTCCAGTTGGAGGGTCT | GCGATCGTCACTGTTCTCCATCACAGATGACATGGAAAATAAGC |
| NITT_091 | chr18AAGACTCGGCAGCATCTCCATAAAAGTGCCTTTGAACTCTGAC TA | GCGATCGTCACTGTTCTCCACCCATGTGAAATCGCATAGTT |
| NITT_050 | chr21AAGACTCGGCAGCATCTCCACATCCAGGACCTACCATCTTG | GCGATCGTCACTGTTCTCCACAACGCTGGCATTCAAAA |
| NITT_010 | chr21AAGACTCGGCAGCATCTCCACCTTCTCACTCACCTCTTTCTTG | GCGATCGTCACTGTTCTCCAGTGTGCAGAGGAGAGACATGA |
| NITT_011 | chr21AAGACTCGGCAGCATCTCCATGTGTGTGTGTTCTCTACCTTGG | GCGATCGTCACTGTTCTCCATATGAGTAGGTGTCTGGTGTATGA AAA |
| NITT-047 | chr21AAGACTCGGCAGCATCTCCAGCAAATCTGGTACTGGGTATGA | GCGATCGTCACTGTTCTCCATCAGATAGTATGGATAAAGGCAAT GA |
| NITT_006 | chr21AAGACTCGGCAGCATCTCCACAATAATCAGACTTTGCCTTGG | GCGATCGTCACTGTTCTCCACATTAAGGGTCTTAGGGTGGTAAA |
| NITT_049 | chr21AAGACTCGGCAGCATCTCCATCCTGTTGGGGAAATTGG | GCGATCGTCACTGTTCTCCAGAAGATAGAGTTTCTCCTGCATCA |
| NITT_017 | chr21AAGACTCGGCAGCATCTCCAGGAACAGGTGCACACATCA | GCGATCGTCACTGTTCTCCACAGCACTGTCCAGCACTTG |
| NITT_007 | chr21AAGACTCGGCAGCATCTCCACAGCTGTAACCTGCTGAGAAAA | GCGATCGTCACTGTTCTCCAGTCTTAATTCTGCTCAGGAAAAGC |
| NITT_009 | chr21AAGACTCGGCAGCATCTCCAGAACAGCATTCCTCCTCCTAGT | GCGATCGTCACTGTTCTCCATTGAACCATAAATGTCAGCTCTTG |
| NITT_070 | chr21AAGACTCGGCAGCATCTCCACCTCACATGTCTGTGCATTAAAA | GCGATCGTCACTGTTCTCCATTCCCTCTTCACATTCTGCTC |
| NITT_071 | chr21AAGACTCGGCAGCATCTCCAGACACAACATCAGAGGCAATCT | GCGATCGTCACTGTTCTCCACTCTTCAAACAGAGAAAACTTAGA TGA |
| NITT_016 | chr21AAGACTCGGCAGCATCTCCATCAGGGTAGAGAATCAGAATTGG | GCGATCGTCACTGTTCTCCACAGAGATCAACCGGAGAAGTAAA |
| NITT_076 | chr21AAGACTCGGCAGCATCTCCACCACGGATCCACTGCATA | GCGATCGTCACTGTTCTCCAGTTCTCTGTAAGTGAAAGCATCCT AAA |

TABLE 1-continued list of 30 primer pairs composing the chromosome 21 aneuploidy detection MASTR assay

| Amplicon | Chrom | Forw | Rev |
|---|---|---|---|
| NITT_057 | chr21 | AAGACTCGGCAGCATCTCCATCTGGTCTAAATAAAGTCTTCACATCA | GCGATCGTCACTGTTCTCCAGAGGTAGGAAATGCACCATCA |
| NITT_020 | chr21 | AAGACTCGGCAGCATCTCCACAGAGGCCATGCCAGTAGT | GCGATCGTCACTGTTCTCCAGAAAGTCTGGGAGGTTGAAGC |
| NITT_039 | chr21 | AAGACTCGGCAGCATCTCCATGCCATCAGAACCCGTAAA | GCGATCGTCACTGTTCTCCACACACAGAAGCACAGGAAAATC |
| NITT_059 | chr21 | AAGACTCGGCAGCATCTCCACCTTCTCTGCCTCCATTCTAGT | GCGATCGTCACTGTTCTCCATAGTGTCCGATAATGAAGAACAGTAAA |
| NITT_053 | chr21 | AAGACTCGGCAGCATCTCCATGGCTAAGCACATACCCTTAAA | GCGATCGTCACTGTTCTCCACTGACACAAATGAAGGCAAAA |
| NITT_044 | chr21 | AAGACTCGGCAGCATCTCCATCTCCATTCCTTCTGCTCTTAGT | GCGATCGTCACTGTTCTCCAGAACTCACTCTGGAAGCAATGA |
| NITT_072 | chr21 | AAGACTCGGCAGCATCTCCAGAAAGCTGGGCGTATTGG | GCGATCGTCACTGTTCTCCAGAACATTCTGAACATCTGGAATGA |

2. MASTR Assay Principle

Primerpairs were first tested in simplex PCR reactions on 20 ng of genomic DNA using 10 pmol per primer; the other parameters were equal to those of the multiplex PCR. The multiplex PCR reactions were performed on 50 ng genomic DNA in a 25-ml reaction containing Titanium™ Taq PCR buffer (Clontech, Palo Alto, Calif.) with a final concentration of 0.25 mM for each dNTP (Invitrogen, Carlsbad, Calif.) and a total of 0.125 ml of Titanium™ Taq DNA Polymerase (Clontech). Primer concentrations were optimized and varied between 0.05 pmol/ml and 0.2 pmol/ml final concentration.

The final multiplex assay (MASTR assay) was used to amplify all DNA samples. The first PCR reaction was performed on 50 ng of DNA with following settings: initial sample denaturation 10 min at 95° C. followed by 20 cycles each consisting of: 45 sec at 95° C., 45 sec at 60° C. and 2 min at 68° C. ending with a final extension step of 10 min of 72° C. (see FIG. 5).

The resulting PCR fragments were 1000 times diluted followed by a second PCR step to incorporate the individual barcode. The PCR conditions of this step are identical to the conditions of the first PCR step (see FIG. 6).

The resulting barcoded amplicons are equimolarly mix and used in an emulsion PCR reaction as described by the manufacturer (Roche diagnostics).

REFERENCES

[1] Lo Y, Corbetta N, Chamberlain P, Rai V, Sargent I, Redman C, and Wainscoat J (1997) Presence of fetal DNA in maternal plasma and serum. The Lancet 350: 485-487

[2] Poon L, Leung T, Lau T, Lo Y (2000) Presence of fetal RNA in maternal plasma. Clin Chem 46: 1832-1834

[3] Ng E, Tsui N, Lau T, Leung T, Chiu R, Panesar N, et al. (2003) mRNA of placental origin is readily detectable in maternal plasma. PNAS 100: 4748-4753

[4] Lo Y, Tsui N, Chiu R, Lau T, Leung T, Heung M, et al. (2007) Plasma placental RNA allelic ratio permits non-invasive prenatal chromosomal aneuploidy detection. Nat Med 13:218-23

[5] Tsui N,2, Wong B, Leung T, Lau T, Chiu R and Lo Y (2009) Non-invasive prenatal detection of fetal trisomy 18 by RNA-SNP allelic ratio analysis using maternal plasma SERPINB2 mRNA: a feasibility study. *Prenat Diagn* 29: 1031-1037

[6] Yang Y, Ding J, Lee M, Loria O, Mohsenian F, Tang M, et al. (2008) Identification of mRNA-SNP markers for a noninvasive prenatal trisomy 21 (T21) test. Prenat Diagn 2008: 28-S12

[7] Chim S, Tong Y, Chiu R, Lau T, Leung T, Chan L, et al. (2005) Detection of the placental epigenetic signature of the maspin gene in maternal plasma. PNAS 102: 14753-14758

[8] Chan K, Ding C, Gerovassili A, Yeung S, Chiu R, Leung T et al. (2006) Hypermethylated RASSF1A in Maternal Plasma: A Universal Fetal DNA Marker that Improves the Reliability of Noninvasive Prenatal Diagnosis. Clin Chem 52: 2211-2218

[9] Lo D, Chan A, Sun H, Chen E, Jiang P, Lun F et al. (2010) Maternal Plasma DNA Sequencing Reveals the Genome-Wide Genetic and Mutational Profile of the Fetus. *Sci Transl Med* 2: 6

[10] Dhallan R, Guo X, Emche S, Damewood M, Bayliss P, Cronin M et al. (2007) A non-invasive test for prenatal diagnosis based on fetal DNA present in maternal blood: a preliminary study. Lancet 369: 474-481

[11] Lo D, Lun F, Chan A, Tsui Y, Chong C, Lau T, et al. (2007) Digital PCR for the molecular detection of fetal chromosomal aneuploidy. PNAS 104:13116-131121

[12] Ehrich M, Deciu C, Zwiefelhofer T; Tynan J, Cagasan L, Tim R et al. (2011) Noninvasive detection of fetal trisomy 21 by sequencing of DNA in maternal blood: a study in a clinical setting. Am J Obstet Gynecol 204:205.e1-11

[13] Sehnert A, Rhees B, Comstock D, de Feo E, Heilek G,1 Burke J and Raval P (2011) Optimal Detection of Fetal Chromosomal Abnormalities by Massively Parallel DNA Sequencing of Cell-Free Fetal DNA from Maternal Blood. Clin Chem 57: 1042-1047

[14] Chen E, Chiu R, Sun H, Akolekar R, Chan A, Leung T et al. (2011) Noninvasive Prenatal Diagnosis of Fetal Trisomy 18 and Trisomy 13 by Maternal Plasma DNA Sequencing. PLoS ONE 6: e21791

[15] Liao G, Lun F, Zheng Y, Chan A, Leung T, Lau T et al. (2011) Targeted Massively Parallel Sequencing of Maternal Plasma DNA Permits Efficient and Unbiased Detection of Fetal Alleles. Clin Chem 57: 92-101

The invention claimed is:

1. A method for the detection of a fetal chromosomal aneuploidy in a pregnant female comprising i) receiving a biological sample from said pregnant female, ii) preparing nucleic acids from said biological sample, iii) amplifying a selected set of target DNA sequences in at least one quantitative multiplex PCR reaction wherein at least one amplified DNA sequence comprises at least one SNP for which the female is heterozygous, iv) sequencing the amplified target DNA sequences, and v) calculating the sum of read counts for all amplified DNA sequences of a suspected chromosomal aneuploidy followed by normalization, against the sum of read counts for all amplified DNA sequences of a reference chromosome to determine by statistical methods a set score indicative for the presence of a fetal chromosomal aneuploidy.

2. The method according to claim 1, wherein said fetal chromosomal aneuploidy is chromosome 13, chromosome 18, chromosome 21, chromosome X, chromosome Y, or combinations thereof.

3. The method according to claim 1, wherein said biological sample is maternal blood, plasma, urine, cerebrospinal fluid, serum, saliva or transcervical lavage fluid.

4. The method according to claim 1, wherein the amplified DNA sequences have a size between 30-180 base pairs.

5. The method according to claim 1, wherein cell stabilizing chemicals are used in the preparation of nucleic acids.

6. The method according to claim 1, wherein the GC content of the target DNA sequences is between 20 and 70%.

7. The method according to claim 1, wherein a size fractionation is used in the preparation of the nucleic acids.

8. The method according to claim 1, wherein the amplified DNA sequences are obtained in a single PCR reaction.

9. The method according to claim 8, wherein the single PCR reaction is a single multiplex PCR reaction comprising more than 40 amplified DNA sequences.

10. The method according to claim 8, wherein the single PCR reaction is a single multiplex PCR reaction comprising more than 60 amplified DNA sequences.

* * * * *